(12) United States Patent
Serex et al.

(10) Patent No.: US 12,390,301 B2
(45) Date of Patent: Aug. 19, 2025

(54) METHOD FOR LABELLING A DEVICE AND DEVICES OBTAINABLE THEREFROM

(71) Applicant: ECOLE POLYTECHNIQUE FEDERALE DE LAUSANNE (EPFL), Lausanne (CH)

(72) Inventors: Ludovic Serex, Chavannes-Renens (CH); Nicolas Vachicouras, Chambesy (CH); Benoit Huguet, Chavannes-Renens (CH); Florian Fallegger, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 203 days.

(21) Appl. No.: 18/008,596

(22) PCT Filed: Apr. 30, 2021

(86) PCT No.: PCT/EP2021/061413
§ 371 (c)(1),
(2) Date: Dec. 6, 2022

(87) PCT Pub. No.: WO2022/017655
PCT Pub. Date: Jan. 27, 2022

(65) Prior Publication Data
US 2023/0248471 A1     Aug. 10, 2023

(30) Foreign Application Priority Data

Jul. 21, 2020   (EP) .................................... 20186896

(51) Int. Cl.
*A61B 90/92*     (2016.01)
*A61B 5/293*     (2021.01)
(52) U.S. Cl.
CPC .............. *A61B 90/92* (2016.02); *A61B 5/293* (2021.01); *A61B 2562/046* (2013.01);
(Continued)

(58) Field of Classification Search
CPC ... A61B 90/92; A61B 5/293; A61B 2562/046; A61B 2562/08; A61B 2562/125;
(Continued)

(56) References Cited

U.S. PATENT DOCUMENTS 6,304,231 B1   10/2001  Reed
2018/0087193 A1*  3/2018  Fu ......................... A61B 5/742

FOREIGN PATENT DOCUMENTS

JP     H1083139 A      3/1998
WO    2010023577 A1   3/2010

OTHER PUBLICATIONS

Machine translation of JPH1083139A (Year: 1998).*

* cited by examiner

*Primary Examiner* — S. Behrooz Ghorishi
(74) *Attorney, Agent, or Firm* — Andrew D. Dorisio; Dickinson Wright PLLC

(57) ABSTRACT

A method for labelling a portion of a device includes the steps of providing a first substrate layer of a transparent or translucent material, depositing a first coloured material onto the first substrate layer in a labelling portion of the layer, thereby obtaining a labelling item, and coupling the labelling item to the device. The method is particularly suitable for producing labelled stretchable devices such as soft body-implantable devices for sensing a physiological signal and/or stimulating an electrical and/or pharmacological activity of a body tissue or organ in a subject.

13 Claims, 8 Drawing Sheets

(52) U.S. Cl.
CPC ..... *A61B 2562/08* (2013.01); *A61B 2562/125* (2013.01); *A61B 2562/164* (2013.01)

(58) Field of Classification Search
CPC ............ A61B 2562/164; A61N 1/0531; A61N 1/0551; A61N 1/37223; A61N 1/37514
USPC .................................................. 156/60, 277
See application file for complete search history.

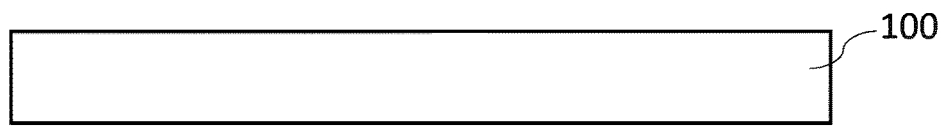
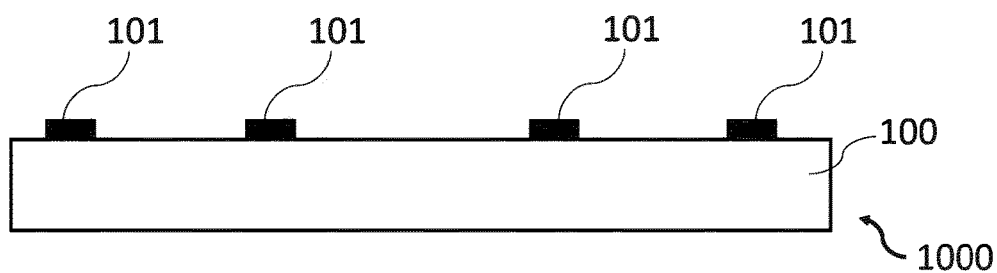
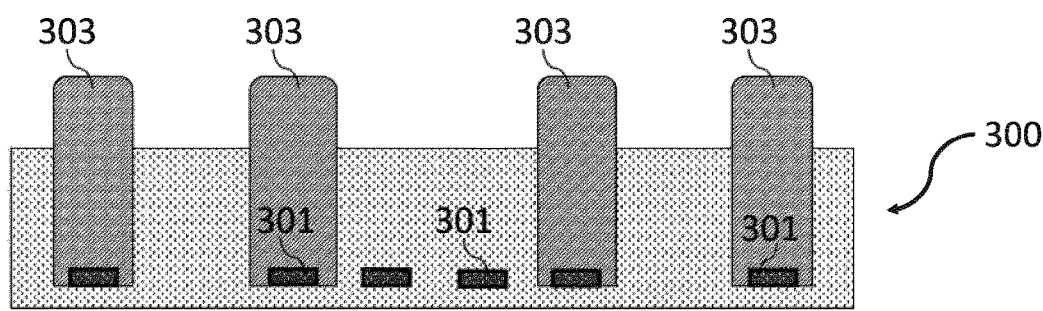
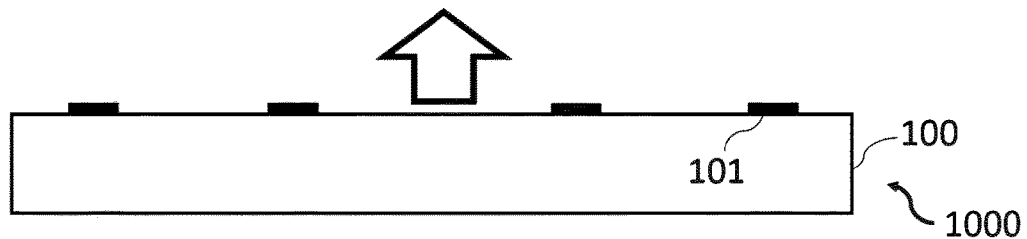
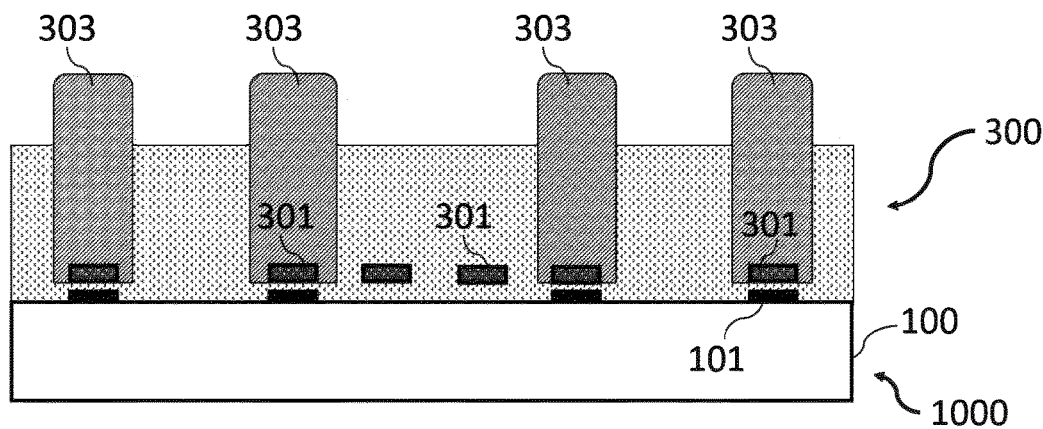

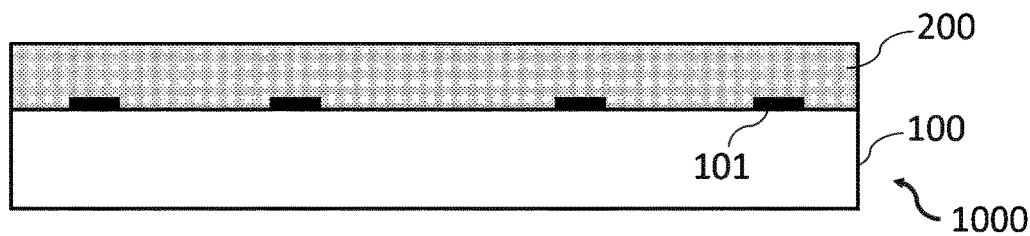
FIG. 3A
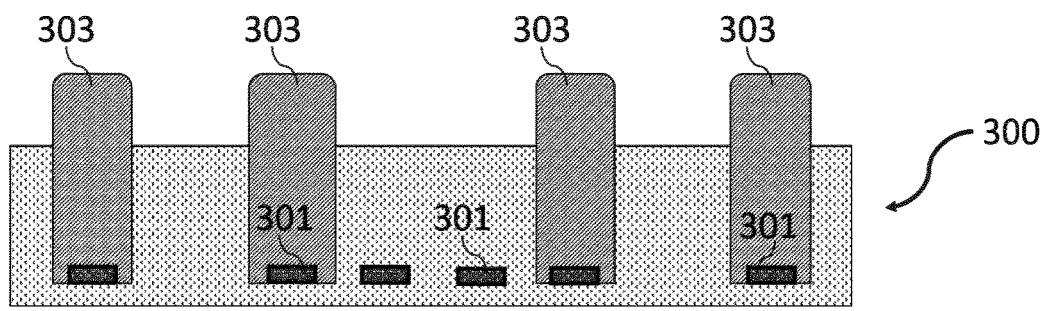
FIG. 3B
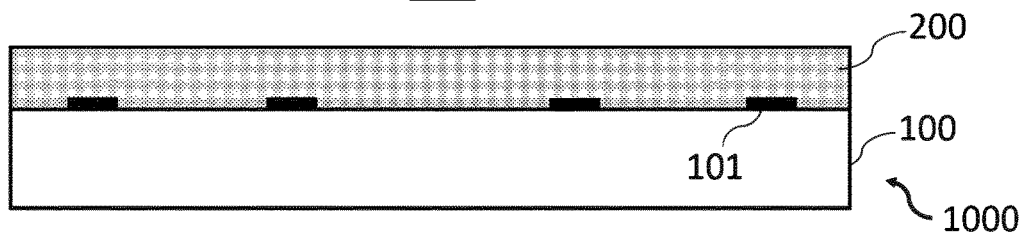
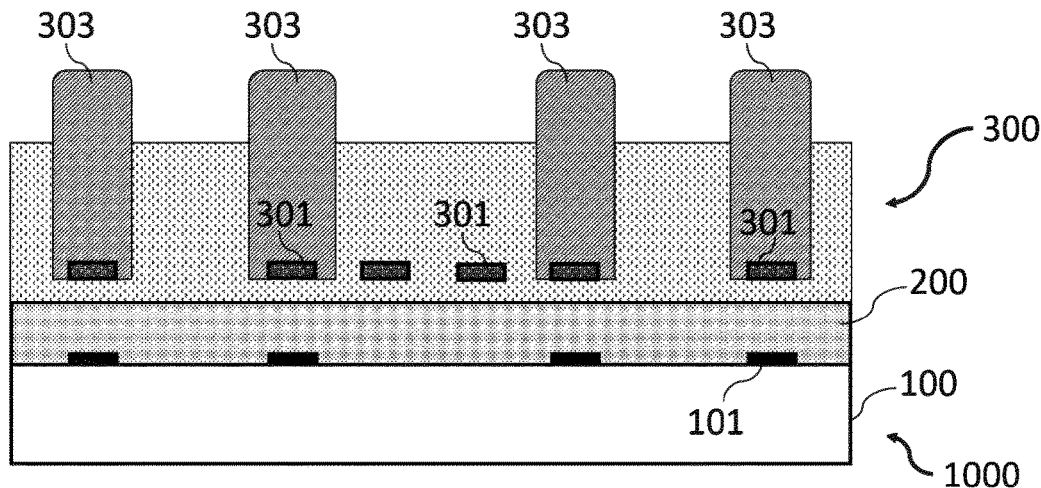
FIG. 3C

FIG. 4A
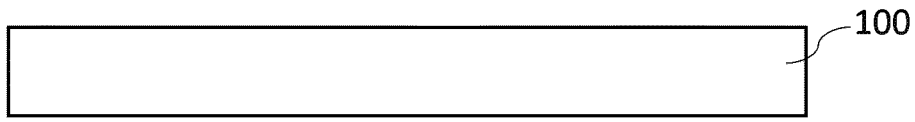
FIG. 4B
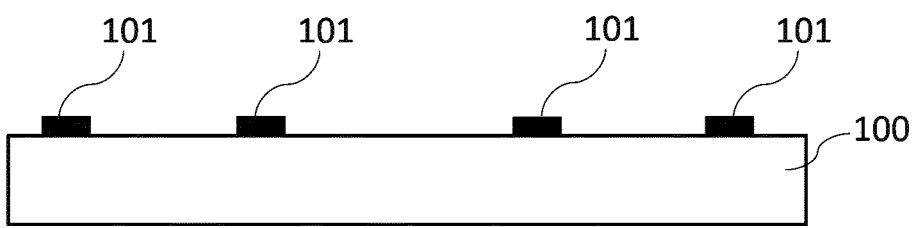
FIG. 4C
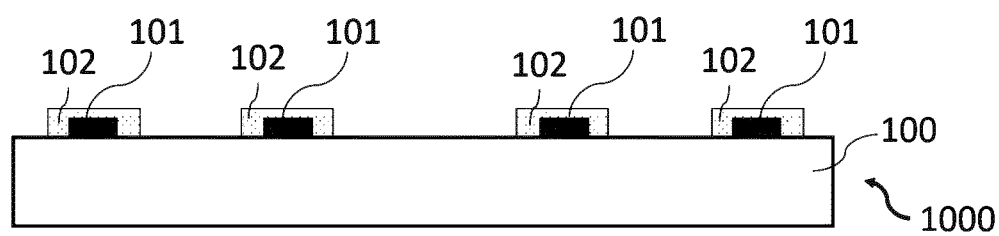
FIG. 4D
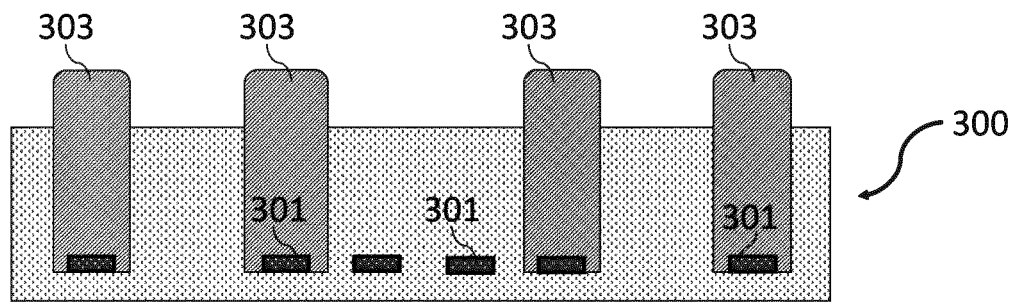
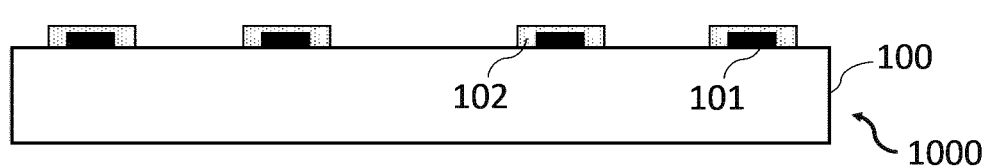

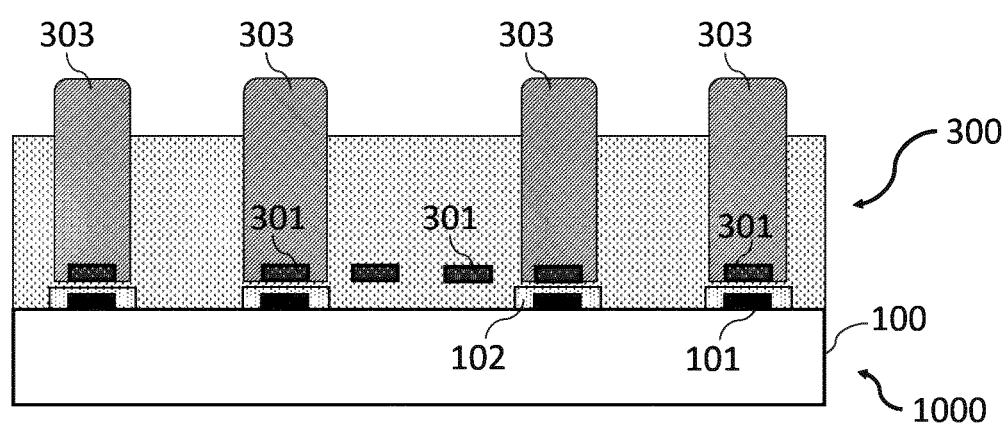

METHOD FOR LABELLING A DEVICE AND DEVICES OBTAINABLE THEREFROM

TECHNICAL FIELD

The present invention relates to a method for labelling portions of a device, such as stretchable device, and to the device obtained therefrom. In particular, the invention discloses a method of the type mentioned above for labelling a biomedical device and to the labelled biomedical device.

BACKGROUND ART

In functional neurosurgery, surgeons use functional devices typically including strips or grids of electrodes that are placed onto the surface of the brain or spinal cord to monitor the activity of the tissue, with the help of a neuromonitoring team that drives the electrodes with appropriate electrical pulses and record activity from the underlying tissue. This functional mapping helps the surgeon identify regions of the brain and help her/him during the surgery. The neuromonitoring team tells the surgeon on which electrode they see activity, which helps the surgeon identify region(s) of the brain in a first time and stop her/his action if functional parts of the brain are being damaged.

As of today, neural implants that are used for neuromonitoring or epilepsy detection are equipped with clear numbering (FIG. 1). They mainly serve two purposes:

1) They crucially help the surgeon in placing the implant in the right orientation (electrode on the tissue and the numbering facing them), and
2) They facilitate the communication between the neuromonitoring team (that does the measurement on the electrode) and the surgeon (that manipulate the implant and that needs a functional feedback on the region where the implant is placed).

This conversation between the surgeon and the neuromonitoring team must be seamless to avoid any mistakes. As the neuromonitoring team do not see the implant, the only thing making sure the surgeon and neuromonitoring team are talking about the right electrode is the ability of the surgeon to properly see the numbering on the electrode.

As of today, most clinically available implants are manufactured manually, and disks 40 (FIG. 1) with numbers 41 on the backside are placed over each electrode. While providing quite nicely contrasted numbering, this method is very labour-intensive and not always possible to implement, especially with new manufacturing techniques being developed. Indeed, with new manufacturing processes and novel implantable devices, particularly stretchable devices, this way of numbering electrodes is not appropriate.

To overcome these limitations, two alternative strategies have been adopted: either completely abandoning numbering, or alternatively placing a number above each electrode. The first strategy, for what said above, is very limiting and risky for the use of implantable devices for neuromonitoring. As for numbering above the electrodes, this approach can become ambiguous (which is not desirable in such surgeries) and because of the reddish background (brain tissue) the electrodes are used on, the contrast is often very bad, extremely impairing the readability.

Despite the development and adoption of stretchable electronic devices, such as compliant sensors, compliant touch interfaces, in vitro electromechanical platforms or soft bioelectronic interfaces (like cortical and spinal cord interfaces) have exploded in the last decade, there is still a need to find an easy and appropriate method to advantageously labelling portions thereof.

SUMMARY OF INVENTION

In order to address and overcome at least some of the above-mentioned drawbacks of the prior art solutions, the present inventors developed a method for labelling portions of devices, such as stretchable ones, having improved features and capabilities.

In particular, a first purpose of the present invention is that of providing a convenient method for labelling any portion of a device, such as a stretchable device, and particularly functional elements thereof.

This aim has been accomplished with the present invention, as described herein and in the appended claims.

In view of the above-summarized drawbacks and/or problems affecting devices of the prior art, according to the present invention there is provided a method for labelling a portion of a device.

The method provides labelling at least a portion of a device by:
  Providing a first substrate layer of a transparent or translucent material;
  Depositing a first coloured material onto the first substrate layer in a labelling portion of the layer, thereby obtaining a labelling item; and
  Coupling the labelling item to the device.

The device is for instance an active or a passive electronic device.

The labelling portion may include a plurality of labelling regions with a predetermined arrangement in the first substrate layer.

The arrangement of labelling regions on the first substrate layer may correspond to the arrangement of items to be labelled onto the device. For instance, but not exclusively, items to be labelled onto the device may be electrodes.

The first coloured material is deposited in the plurality of labelling regions to obtain a plurality of labels in the labelling item.

The plurality of labels, therefore, are arranged in the labelling item to match the items of the device to be labelled, for instance the electrodes, when the labelling item is coupled to the device.

The labelling item may have a same size of the at least one portion of the device to be labelled.

The labelling item may have a same stretch-ability of the at least one portion of the device to be labelled, so as changes in distances and/or arrangement of items of the device as a consequence of stretching the device may be followed labels due to same changes in distances and/or arrangement of labels in the labelling item.

Moreover, according to a further aspect of the method of the present invention, the device is manufactured subsequently with respect to the step of first coloured material onto the first substrate layer in a labelling portion of the layer, thereby obtaining the labelling item. Accordingly, coupling the device to the labelling item encompass manufacturing the device on the labelling item. In this case, matching the labels of the labelling items to the items of the device is made by manufacturing each of a plurality of items of the device onto a corresponding one label among a plurality of labels of the labelling item already manufactured.

In an embodiment, manufacturing each of said plurality of items of the device comprise manufacturing the plurality of items of the device on a second substrate layer which is in turn arranged on the first substrate layer and the labels thereof.

Another object of the present invention relates to a labelled device obtainable by a method of the invention.

Further embodiments of the present invention are defined by the appended claims.

The above and other objects, features and advantages of the herein presented subject-matter will become more apparent from the following description with reference to the attached figures showing some preferred aspects of said subject-matter.

BRIEF DESCRIPTION OF DRAWINGS

FIG. 2A-2D schematically represents steps of a method for labelling a device according to an embodiment of the present disclosure;

FIG. 3A-3C schematically represents steps of a method for labelling a device according to a second embodiment of the present disclosure;

FIG. 4A-4E schematically represents steps of a method for labelling a device according to a third embodiment of the present disclosure;

DETAILED DESCRIPTION OF THE INVENTION

Figure 1:
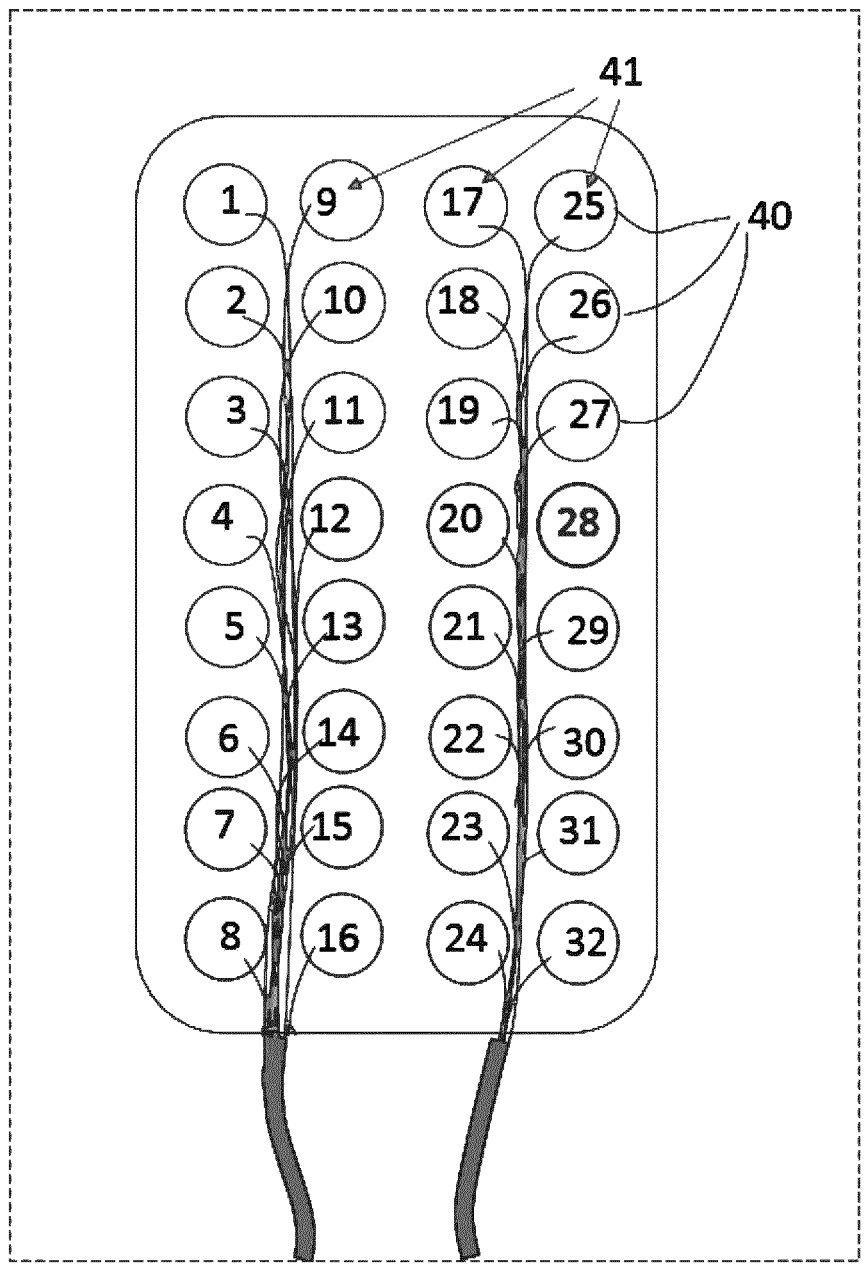
FIG. 1 schematically represents a labelled device according to the prior art.

The subject-matter described in the following will be clarified by means of a description of those aspects which are depicted in the drawings. It is however to be understood that the scope of protection of the invention is not limited to those aspects described in the following and depicted in the drawings; to the contrary, the scope of protection of the invention is defined by the claims. Moreover, it is to be understood that the specific conditions or parameters described and/or shown in the following are not limiting of the scope of protection of the invention, and that the terminology used herein is for the purpose of describing particular aspects by way of example only and is not intended to be limiting.

Unless otherwise defined, technical and scientific terms used herein have the same meaning as commonly understood by one of ordinary skill in the art to which this invention belongs. Further, unless otherwise required by the context, singular terms shall include pluralities and plural terms shall include the singular. The methods and techniques of the present disclosure are generally performed according to conventional methods well known in the art and as described in various general and more specific references that are cited and discussed throughout the present specification unless otherwise indicated. Further, for the sake of clarity, the use of the term "about" is herein intended to encompass a variation of +/−10% of a given value.

Non-limiting aspects of the subject-matter of the present disclosure will be described by way of example with reference to the accompanying figures, which are schematic and are not intended to be drawn to scale. For purposes of clarity, not every component is labelled in every figure, nor is every component of each aspect of the invention shown where illustration is not necessary to allow those of ordinary skill in the art to understand the invention.

The following description will be better understood by means of the following definitions.

As used in the following and in the appended claims, the singular forms "a", "an" and "the" include plural referents unless the context clearly dictates otherwise. Also, the use of "or" means "and/or" unless stated otherwise. Similarly, "comprise", "comprises", "comprising", "include", "includes" and "including" are interchangeable and not intended to be limiting. It is to be further understood that where for the description of various embodiments use is made of the term "comprising", those skilled in the art will understand that in some specific instances, an embodiment can be alternatively described using language "consisting essentially of" or "consisting of."

In the frame of the present disclosure, the expression "operatively connected" and similar reflects a functional relationship between the several components of the device or a system among them, that is, the term means that the components are correlated in a way to perform a designated function. The "designated function" can change depending on the different components involved in the connection. Likewise, any two components capable of being associated can also be viewed as being "operably couplable," to each other to achieve the desired functionality. Specific examples of operably couplable include but are not limited to physically mateable and/or physically interacting components and/or wirelessly interactable and/or wirelessly interacting components and/or logically interacting and/or logically interactable components. A person skilled in the art would easily understand and figure out what are the designated functions of each and every component of the device or the system of the invention, as well as their correlations, on the basis of the present disclosure.

The expression "conductive track" refers to any film, path, stripe, strand, wire or the like which is electrically conductive in nature. For the sake of clarity, the word "electrode" is herein used to mean the distal part of a conductive track which may be in direct contact with an external item, such as a subject's tissue. However, in embodiments of the invention, the term "electrode" is used to mean either or both a conductive track and/or its distal, terminal portion configured to interface with a biological tissue. Conductive tracks according to the present disclosure are used to connect and/or close an electrical circuit, and are thus usually electrical connectors or "interconnects". A conductive track is generally a metallic element that conducts an electric current toward or away from an electric circuit, but can be made of any suitable electrically conductive material, including but not limited to metals such as Au, Pt, Al, Cu and the like, as well as any alloy, oxides and/or combinations thereof; conductive polymeric materials; composite material such as polymeric materials embedding metal particles and/or metal strands or stripes, including insulating materials functionalized with electrically conductive flakes or fibres, for example carbon-filled polymers; liquid metals, including alloys or oxides thereof, such as gallium; electrically conductive inks; as well as any suitable combination thereof. Photo-lithography, particle implantation, laser pattering, material evaporation, screen printing and/or micro-integrated electronics, among other techniques readily available in the art, can be adopted to fabricate the components of the electrodes.

The expressions "film" or "thin film" relate to the thin form factor of an element of the device of the invention such as a support substrate and/or a conductive track. Generally speaking, a "film" or "thin film" as used herein relates to a layer of a material having a thickness much smaller than the other dimensions, e.g. at least one fifth compared to the other dimensions. Typically, a film is a solid layer having an upper surface and a bottom surface, with any suitable shape, and a thickness generally in the order of nanometers, micrometers or even millimetres, depending on the needs and circumstances, e.g. the manufacturing steps used to produce it. In some embodiments, films according to the invention have a thickness comprised between 1 nm and 10 mm, such as between 1 nm and 10 nm, 20 nm and 100 nm, 5 µm and 5 mm, between 5 µm and 1 mm, between 10 µm and 1 mm, between 5 µm and 500 µm, between 50 µm and 500 µm between, between 50 µm and 150 µm, 100 µm and 500 µm or between 200 µm and 500 µm. When referring to thin electrode films, those can have a thickness comprised between 1 nm and 500 µm, such as between 20 nm and 200 nm or between 50 nm and 100 nm. These dimensions are considered to be optimal in the frame of the present invention for what concerns stretchability and mechanical compliance of the device meant to be interfaced with body tissues The term "compliant", when referred to an item such as an electrode, track and/or interconnect, refers to the behaviour of said conductive element to adapt to change its shape according to the shape change of the support it adheres to, without substantially compromising mechanical and/or electrical performances. The term "compliant" is intended to include any conformable structure which is compressible, reversibly compressible, elastic, flexible, bendable, stretchable or any combination thereof. Examples of compliant electrodes known in the art include metal thin-films (including patterned electrodes, out-of-plane buckled electrodes, and corrugated membranes), metal-polymer micro/nanocomposites, carbon powder, carbon grease, conductive rubbers or conductive paints, a review of which is provided in Rosset and Shea (Applied Physics A, February 2013, Volume 110, Issue 2, 281-307), incorporated herein in its entirety by reference. As it will be apparent to those skilled in the art, built-in multilayers or stacks of several layers of any of the above polymeric, composite, metallic and/or oxide materials, as well as combinations thereof, are encompassed in the definition of compliant interconnect. Preferably, but not limited to, the electrodes, tracks and/or interconnects according to the invention are compliant in nature. Preferably, but not limited to, the electrodes, tracks and/or interconnects according to the invention are stretchable in nature. In some embodiments, stretchable electrodes as the ones described in International Patent Applications WO 2004/095536, WO 2016/110564 and/or WO 2018/100005A1, incorporated herein in their entirety by reference, can be used.

In the frame of the present invention, "physical and/or mechanical properties" means, by way of examples, stress-strain behaviour, elastic modulus, fracture strain, conformability to curvilinear surfaces, compliance to soft surfaces, thickness, area and shape which, in a set of embodiments according to the invention, have to be as similar as possible to those to be found in tissues of a subject's body.

The term "soft" is herein meant to include any material that is compressible, reversibly compressible, elastic, flexible, stretchable or any combination thereof. Particularly, a soft material includes materials having a small Young's modules (typically of <100 MPa, such as between 0.01 and 100 MPa), providing a large elongation and/or compression upon a strain and/or a compression stress, typically of >5% of the elongation/compression of a soft structure at rest. In such a way, the obtained device is highly compliant even for thickness of several millimetres to centimetres upon experiencing a deformation. Generally speaking, "deformation" may refer to any compression, expansion, contraction, bending, torsion, linear or area strain experienced by at least a portion of a structure or a substrate according to the present disclosure.

A soft material may be substantially made of a soft polymeric material, or combinations of many soft polymeric materials, possibly biocompatible ones, whenever needed, to fit with biomedical applications herein disclosed.

In preferred aspects according to the present disclosure, soft materials are stretchable, i.e. elastically deformable upon elongation, preferably in more directions. As used herein, the term "stretchable" refers to the elastic behaviour of an item. In particular, a stretchable item can withstand an elongation or multidirectional strain, upon a single or multiple cycles, comprised between 1 and 500%, preferably at least 5%, such as about 50%, about 100% or about 200%, of its size at rest without cracking or loss of its physical and/or mechanical properties, which represents an advantage in those contexts and/or body structures in which several cycles of mechanical stresses over time can be foreseen.

Examples of soft materials comprise for instance thermosets or thermoplastics such as styrene butadiene styrene (SBS) or styrene ethylene butylene styrene (SEBS), soft foams such as polyurethanes including reticulated polyurethanes, polyvinyl chloride (PVC), neoprene, uncrosslinked neoprene, cross-linked polyethylene, polyether, ethylene-vinyl acetate (EVA), polyethylene-vinyl acetate (PEVA), polypropylene glycol (PPG), latex, elastomeric materials such as silicone rubber (e.g. polydimethylsiloxane PDMS) or fluorosilicone rubber, thermoplastic elastomers such as styrenic block copolymer (SBC), ethylene propylene diene monomer (EDPM) rubber, butyl rubber, nitrile rubber, or combinations of any of the foregoing.

In some context, particularly for biomedical application, a soft material may also comprise, or being substantially composed of, one or more compounds selected from a non-exhaustive list comprising natural polymeric material (i.e., non-synthetic polymers, polymers that can be found in nature) and/or polymers derived from the Extra Cellular Matrix (ECM) as gelatin, elastin, collagen, agar/agarose, chitosan, fibrin, proteoglycans, a polyamino-acid or its derivatives, preferably polylysin or gelatin methyl cellulose, carbomethyl cellulose, polysaccharides and their derivatives, preferably glycosaminoglycanes such as hyaluronic acid, chondroitinsulfate, dermatansulfate, heparansulfate, heparine, keratansulfate or alginate, nucleotides, polylipides, fatty acids, as well as any derivative thereof, fragment thereof and any combination thereof.

As it will be appreciated by a person skilled in the art, a soft material may also be a gel or a hydrogel. As used herein, the term "gel" refers to a non-fluid colloidal network or polymer network that is expanded throughout its whole volume by a fluid. The term "hydrogel" refers to a gel in which the swelling agent is water. In the frame of manufacturing of e.g. sensors for biomedical application or implantable neuroprosthetic interfaces, the choice of a soft material and in some instances gels/hydrogel is ideal, particularly for its concomitant ability to tolerate mechanical deformations caused by movements, muscle contractions, and other geometrical changes without experiencing major losses in its performances.

Within the frame of the present invention, the expression "intrinsically not elastic material" has to be understood as meaning a material which, once subjected to strain (pressure, stress, stretching, distorsion or the like) either breaks or is deformed permanently, i.e. without gaining again in a spontaneous and/or natural way, its original shape and dimensions. To the contrary, an "intrinsically elastic material" is a material which, once subjected to strain gains again in a spontaneous and/or natural way its original shape and dimensions.

The term "subject" as used herein refers to animals, including birds and mammals. For example, mammals contemplated by the present invention include human, primates, domesticated animals such as cattle, sheep, pigs, horses, laboratory rodents and the like.

Within the meaning of the present invention, a "fixed implant" defines a biomedical device having the ability to conform to established and/or customised surgical procedures and to reside in vivo without producing adverse biological reactions over extended periods of time, such as for instance over 30 days (so-called "chronic use implant"). Still within the meaning of the present invention, a "removable implant" defines a biomedical device having the ability to conform to established and/or customised surgical procedures and to reside in vivo for a limited amount of time, such as for instance the time of a surgical operation or for a period of time shorter than 30 days (so-called "acute use implant").

With reference to FIGS. 2A-2D, steps of a method for labelling a portion of a device are schematically represented, said method comprising the steps of:
  a) providing a first substrate layer 100 of a transparent or translucent material;
  b) depositing a first coloured material 101 onto said first substrate layer 100 in a labelling portion of said layer; and
  c) coupling said first substrate layer 100 to the device 300, for instance an active or a passive device.

In order to address the drawbacks affecting the prior art, one of the key inventive concepts characterizing the method of the invention relies in the exploitation of a layer-based manufacturing method to provide labelling coloured layer(s) comprising a coloured material in correspondence of a labelling portion of a so-obtained labelling item 1000. A "labelling item" according to the invention is composed at least of the first substrate layer 100 of transparent or translucent material, and of the first coloured material 101 located onto said first substrate layer 100, in the labelling portion thereof. Such a labelling item 1000 is depicted in an exemplary embodiment in FIG. 2B. The labelling item 1000 according to the invention can further comprise in embodiments of the invention at least a second substrate layer, a second or further coloured material(s) or combinations of the foregoing, as exemplarily depicted in FIG. 3C or 4D.

Once the labelling item 1000 is ready, this is coupled to the active or passive device 300. To this aim, various methods and means for coupling may be envisaged, depending on the needs and circumstances, such as for instance the nature of the device to be coupled with the labelling item 1000, which will be described later on in more details.

As depicted in FIG. 2A, during a first method step, the first transparent or translucent substrate layer 100 is provided. The first substrate layer 100 may be composed of a soft material, for example an intrinsically elastic material, such as an elastomeric material. As a way of example, an elastomeric substrate may be a PDMS substrate.

To this aim, in embodiments of the invention a soft curable material is provided upon or within a temporary substrate with method known in the art such as overmolding, spray coating, dispensing (pouring), forming, compression molding, dip coating and the like and subsequently cured. The term "curing" is herein used to refer to the toughening or hardening of a polymer material by cross-linking of monomer chains into a polymer, brought about by electron beams, heat, UV radiation and/or chemical additives such as crosslinkers, as well known by a person skilled in the art.

Still by way of non-limiting example, providing the substrate layer 100 may comprise spin coating and/or blade coating a PDMS layer on a carrier (not depicted), for instance a silicon carrier (wafer or the like), curing the layer at e.g. 80° C. and removing the carrier. The thickness of the substrate layer 100 may range for instance from 500 nm up to several millimetres, such as for instance between 1 µm and 1 mm, according to the needs and/or circumstances.

During a second step, as depicted in FIG. 2B, the first coloured material 101 is placed on the substrate layer 100. By way of example, the first coloured material 101 may be an ink, possibly biocompatible ones depending on the needs, provided on the substrate layer 100. At the end of the second step, therefore, the labelling item 1000, comprising the substrate layer 100 having the first coloured material 101 located on specific portions thereof, has been formed.

Coloured materials according to the invention are mainly materials used for labelling purposes only, and are not in direct physical contact with any of the functional elements present on the device which the labelling item 1000 is coupled to or otherwise associated. Accordingly, the coloured materials employed in the frame of the invention are not e.g. conductive inks in operative connection with a conductive track of a coupled device 300, and are located in correspondence of the portion of the device to be labelled without however influencing its performance.

Nonetheless, coloured materials may have optical properties such as fluorescence, phosphorescence and/or radio-opacity to facilitate the visual properties obtainable in different contexts (from interventional radiology to research settings). This may be obtained by including into the coloured material(s) fluorescent or chemiluminescent compounds such as fluorophores or metallic nanoparticles of (a) radiopaque, biocompatible material(s) such as for instance barium sulphate, zirconium oxide, zinc oxide, calcium tungstate, gold, gadolinium, silver, platinum, tantalum, salts thereof and/or oxides thereof.

Advantageously, in certain embodiments, the first coloured material 101 can be provided in the form of a soft polymeric matrix or gel. For instance, the first coloured material 101 can comprise an intrinsically elastic material, such as an elastomeric material. This is of particular interest in situations that require for instance stretchability in one or more directions of the labelling item 1000 to comply with deflections of the coupled device 300, including bending, torsion, elongation and the like.

The first coloured material 101 can be provided on the first substrate layer 100 by screen printing transfer techniques. This technique enables ease of use and scalability of the process for industrialization. As a way of example, one possible implementation for the screen-printing mask is to laminate a PET sheet onto the first substrate layer 100 and laser cut the design. The coloured material 101 can then be screen-printed through the mask and the mask removed. This method allows for fast prototyping and easy design change. A second implementation method is the use of a holder were the substrate 100 can be placed. A metallic screen-printing mask is placed onto the substrate 100 and coloured material 101 can be coated through the mask. The metallic screen-printing mask can then be removed, cleaned and reused later on.

Said first coloured material 101 is deposited onto said first substrate layer 100 to provide one or more of a shape label, a number label, a letter label, a barcode label, a QR-code label, an alignment and/or tracking mark, a background serving as a projection screen and a colour label. The versatility of the method of the invention is prone to be declined in a variety of ways; for instance, it can be envisaged the use of any kind of colour to be placed anywhere on the labelling item 1000, so to label or tag for instance different devices, or differentiate between the same kind of devices to be used for different scopes. It could also be imagined to print serial numbers or bar codes or any identification label to help identifying the devices after its use or for tracking purposes, useful for post market surveillance. It could also be used to create different labels on the same implant in order to differentiate parts of it such as multiple electrode sites and/or multiple outlet and/or light emitting device and/or any other element of an active or a passive coupled device.

In a third method step, as depicted for instance in FIGS. 2C and 2D, the previously obtained labelling item 1000 is coupled to the active or passive device 300. In some embodiments, the step of coupling the labelling item 1000 to the device 300 comprises attaching, bonding, gluing or otherwise connecting said device 300 onto the labelling item 1000. In other embodiments the coupling step comprises manufacturing said device 300 onto the labelling item 1000. As it will be apparent to a skilled person, the above aspects are of course dependent inter alia on the type of device 300 to be labelled, the compatibility of the manufacturing processes of the labelling item and the coupled device and the like. This aspects will be detailed later in the description for certain specific aspects of the invention.

The method according to the invention foresees in certain aspects some additional steps for the manufacturing of the labelling item 1000, without departing from the general inventive concept. For instance, as shown in FIGS. 4A-4E, the method may further comprise a further step of depositing at least a second coloured material 102 onto the first substrate layer 100 and/or onto the first coloured material 101 in the labelling portion of said first substrate layer 100. The so-obtained labelling item 1000, as exemplarily shown in FIGS. 4C and 4D, is comprising the first substrate layer 100 with first coloured material 101 overlaid by the second coloured material 102. The process can be repeated several times to create e.g. stacks of coloured materials or different coloured materials in different labelling portions of the labelling item 1000. This is of particular interest to differentiate the various portions of the coupled device 300, or to enhance the contrast between two coloured materials. As it will be evident, preferably the first and the second coloured materials 101, 102 have different colours. The second coloured material 102 may have the same features of the first coloured material 101 in terms of chemical and/or mechanical characteristics.

Figure 5A:
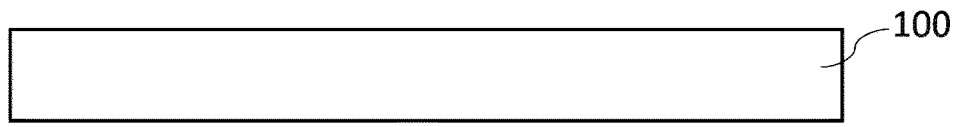
FIG. 5A-5G schematically represents steps of a method for labelling a device according to a fourth embodiment of the present disclosure.
Figure 5B:
Figure 5C:
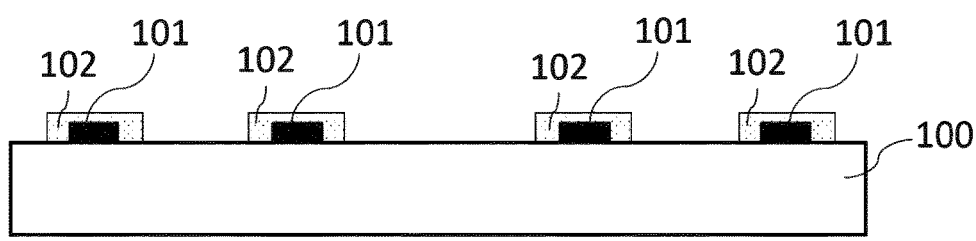
Figure 5D:
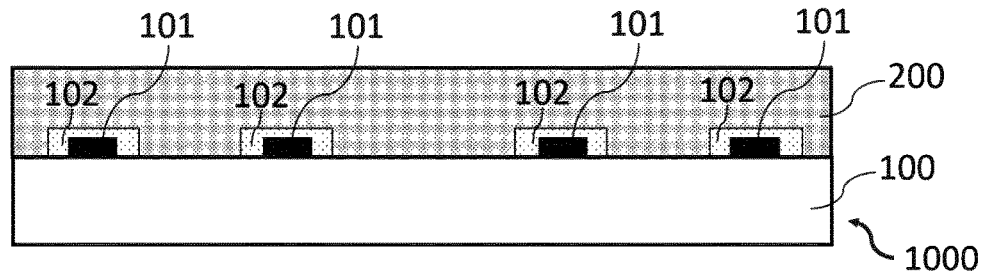
Figure 5E:
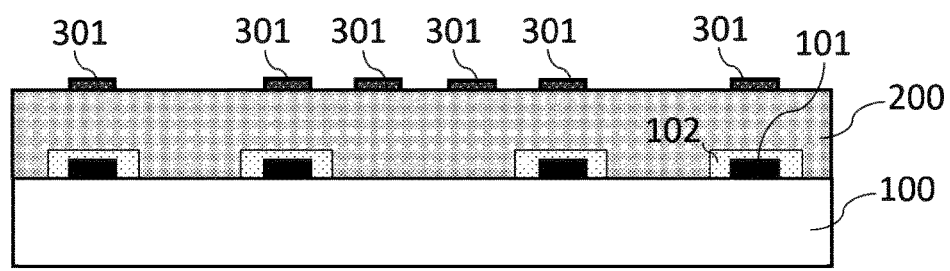

In embodiments of the invention, the method may further comprise a step of applying a second substrate layer 200 onto said first coloured material 101 and said first substrate layer 100. These embodiments are particularly suitable and advantageous in case a direct labelling of the device is wanted by directly manufacturing said device onto a labelling item. In this context, the second substrate 200 may be provided onto the first coloured material 101 and the first substrate layer 100 by methods as previously described including bonding, gluing, overmolding, spray coating, pouring and the like, depending on the needs and circumstances. Said second layer 200 will then act as a substrate for the subsequent production of the device 300 on top of it. This embodiment is exemplarily shown in FIG. 5A-5G: firstly, the labelling item 1000 comprising a first substrate layer 100, first and second coloured materials 101, 102 and a second substrate layer 200 are provided as described (FIGS. 5A to D). In the example given, the second substrate layer 200 is subsequently patterned, in FIG. 5E, with a number of conductive tracks of paths 301. This may be done by deposing a metal such as Au, Pd, Pt, Ir or alloys thereof via e.g. physical vapour deposition such as thermal evaporation or sputtering, chemical vapour deposition, spray coating, lamination, Cluster ion implantation or Supersonic Cluster Beam Implantation. Additionally or alternatively, tracks of paths 301 may be substantially composed of composite materials such a metallic and/or carbon-based inks and pastes deposited by e.g. spray coating, sputtering, screen printing or inkjet printing. Additionally or alternatively, tracks of paths 301 may be substantially composed of liquid metals or alloys thereof, preferably one of gallium and a gallium-based alloy, deposited by e.g. physical vapour deposition, chemical vapour deposition, spray coating, thermal evaporation/condensation, direct writing screen printing, doctor blading or inkjet printing. Combinations of any of the above solutions are also envisageable.

Figure 5F:
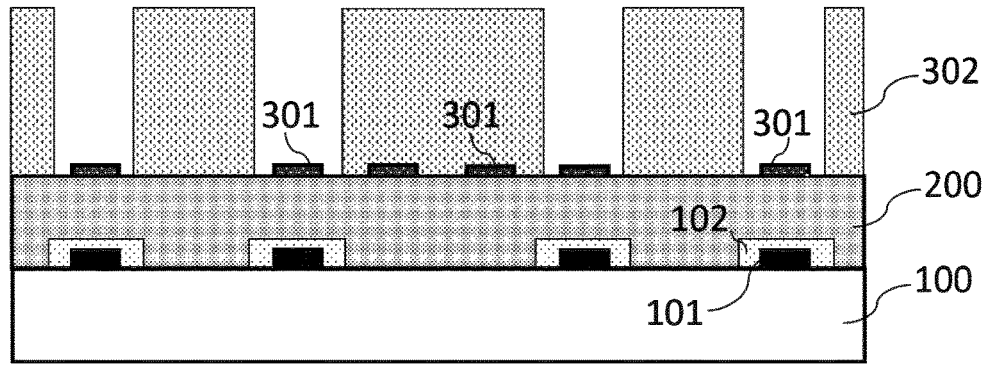
Figure 5G:
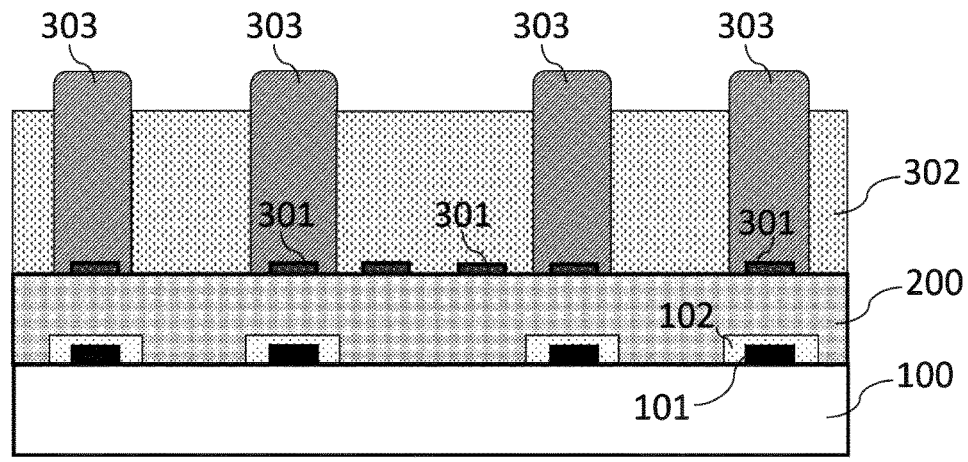

A device substrate 302, which may act for instance as an encapsulation substrate, is subsequently placed on top of the patterned labelling item and structured with methods known in the art such as for instance photostructuration of a dry film resist with a mask (FIG. 5F). Finally, electrode pads 303 are operatively coupled with the tracks 301 by e.g. vacuum metal deposition (FIG. 5G).

The second substrate layer 200 can be made of a transparent or translucent material, and may possibly be composed of an intrinsically elastic material such as an elastomeric material. For example, the second substrate layer 200 can be substantially composed of PDMS.

In the embodiments shown in FIGS. 2 to 5 herewith, a labelling portion of the labelling item 1000, i.e. the portion where a coloured material is placed, is located in correspondence of a functional element of the device 300, in the shown examples (an) electrode pad(s) 303. Nonetheless, depending on the circumstances, said functional element can be an electrode array, a conductive track, a pad, a thru via, a microchip, a reservoir, a connector, a light emitting device, a microfluidic channel, a microfluidic outlet, an array of microfluidic outlets, a mechanical transducer, a chemical sensor and/or an optical device, to cite a few. Accordingly, the method of the invention is at the same time suitable for labelling a portion of a device in a non-functional portion or in a functional portion, thereby permitting a high versatility of the method depending on the needs.

As it will be evident from what said until now, the main advantage of the method according to the invention lies in the possibility of easily labelling a portion of a stretchable electronic device. Particularly, an active or a passive stretchable device 300 substantially made of a soft material, for instance an intrinsically elastic material such as an elastomeric material, may be advantageously labelled in defined portions thereof with the labelling item 1000, and advantageously with the labelling item 1000 being composed in at least the first substrate layer 100, and preferably also in the coloured material(s) 101, 102 and where present the second substrate layer 200, substantially of a soft material, preferably an intrinsically elastic material such as an elastomeric material. In such a way, the labelling item 1000 does not alter in any way the performances of the labelled device 300, while providing a clear and optimal labelling of this latter, as both the labelling item 1000 and the labelled device 300 present the same or very similar physical and/or mechanical properties.

As it will result apparent from the above description, one object of the present invention relates to a labelled device obtainable by a method according to the present disclosure. Any one of the previously-described embodiments concerning the method of the invention, in any combination, can be used to obtain a labelled device. Particularly, a labelled device may comprise a stretchable electronic device 300 labelled by a labelling item 1000 as previously described. A stretchable electronic device 300 may be selected for a non-exhaustive list comprising a sensor, particularly deformable sensors, such as strain sensors or touch sensors; a wearable ("on-body" and/or "on-organ") electronic device; an electrode array for cell culture and tissue slice culture; a sensing robotic skin; a stretchable/deformable antenna; and an implantable device suitable to be used as e.g. a neuroprosthetic interface with the central nervous system, i.e. the spinal cord, brain, or the peripheral nervous systems, i.e. the ganglia and nerves, or soft biological tissue, for instance for the purpose of stimulating and/or recording neurological or cardiac activity or even for stimulating electrical potential of excitable cells or the like.

A stretchable electronic device 300 according to the invention, depending on the needs and the applications, can have any suitable shape, with the most suitable for many of the above-cited applications being a flat, planar shape having a thickness comprised between 1 μm and 10 cm such as between 1 μm and 1 cm, between 1 μm and 1 mm, between 1 and 500 μm, between 1 and 300 μm or between 1 and 100 μm.

Suitable devices may comprise rigid or semi-rigid electronic components such as printed circuit boards (PCBs), flexible circuit boards (FCBs), as well as individual packaged electronic components such as LEDs, IMUs, MCUs, batteries, transistors and the like, and electrical conductors such as electrical conductive strips, paths, lines, arrays or the like, preferably compliant, bendable and/or stretchable in nature.

The electrical conductors may be in contact with both the soft polymeric matrix and the rigid electronic components. Said electrical conductors may have a thickness comprised between about 1 and 1000 nanometers, such as for instance between about 10 and 800 nanometers, between about 50 and 500 nanometers, between about 100 and 600 nanometers, between about 200 and 500 nanometers or between about 300 and 500 nanometers. Furthermore, said electrical conductors can be preferably made of a thin film or layer of a metal such as Au, Pd, Pt, Ir or alloys thereof and/or liquid metals or alloys thereof, preferably but not limited to one of gallium and a gallium-based alloy.

In embodiments, the labelling item 1000 is substantially composed in at least the first substrate layer 100, and preferably also in the coloured material(s) 101, 102 and where present the second substrate layer 200, of a soft material, preferably an intrinsically elastic material such as an elastomeric material. In embodiments, a stretchable electronic device 300 is an active or passive, soft body-implantable device for sensing a physiological signal and/or stimulating an electrical and/or pharmacological activity of a body tissue or organ in a subject.

Accordingly, a soft body-implantable device 300 can be configured as a way of example as a fixed or removable neural or nerve implant, heart implant, kidney implant, pancreatic implant, bladder implant, retina implant or gut implant, to mention some.

A soft body-implantable device 300 may be in one embodiment a peripheral or Central Nervous System (CNS) nerve interface, acting as a bridge between the peripheral/central nervous system and external devices to bi-directionally transducing recorded information and/or sending signals between the human body and a machine processor, and particularly as a fixed or removable implant configured to interface with a nerve or a brain tissue with the purpose of electrically sensing and/or stimulating an electrical activity in a subject.

Figure 6:
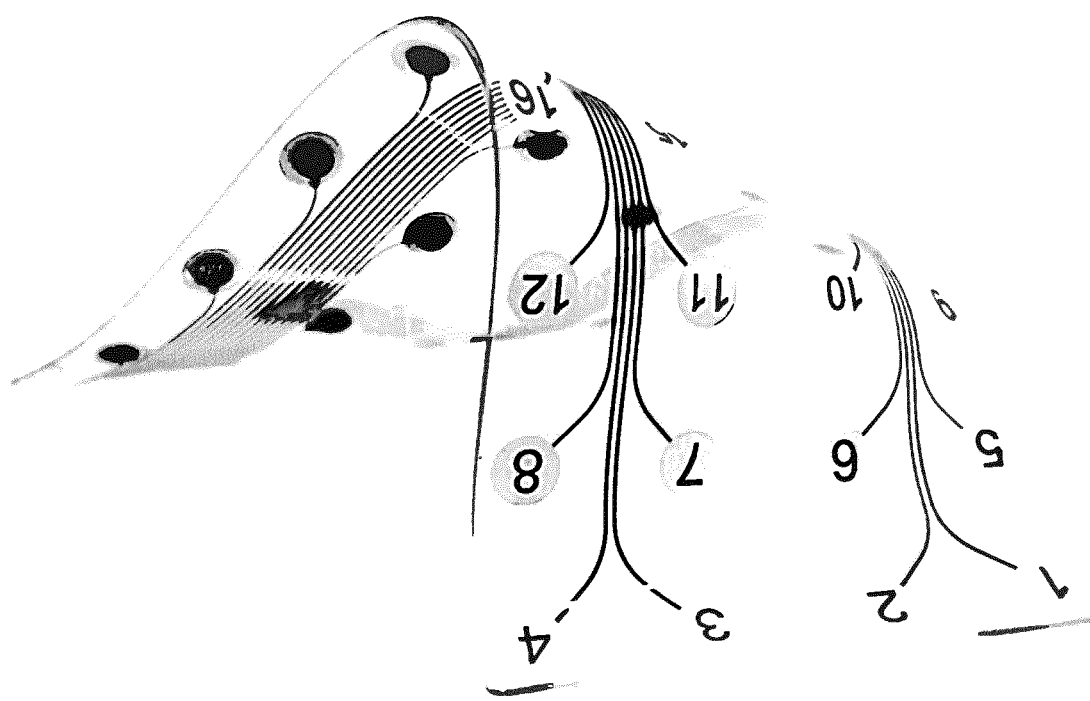
FIG. 6 represents a labelled stretchable cortical grid manufactured according to the method of the present disclosure.

In one embodiment, soft body-implantable device 300 is a cortical grid or stripe comprising a plurality of electrodes, wherein said electrodes are labelled by using the method of the invention. One non-limiting example of a labelled stretchable cortical grid manufactured according to the method of the present disclosure is shown in FIG. 6.

While the invention has been disclosed with reference to certain preferred embodiments, numerous modifications, alterations, and changes to the described embodiments, and equivalents thereof, are possible without departing from the sphere and scope of the invention. Accordingly, it is intended that the invention not be limited to the described embodiments, and be given the broadest reasonable interpretation in accordance with the language of the appended claims.

The invention claimed is:

1. A method for labelling a portion of a device (300), said method comprising the steps of:
    Providing a first substrate layer (100) of a transparent or translucent material;
    Depositing a first colored material (101) onto said first substrate layer (100) in a labelling portion of said first substrate layer, thereby obtaining a labelling item (1000); and
    Coupling said labelling item (1000) to the device (300), wherein said device (300) is manufactured onto said first substrate layer (100).

2. The method of claim 1, further comprising a step of depositing at least a second colored material (102) onto the first substrate layer (100) or the first colored material (101) in a labelling portion of said first substrate layer (100).

3. The method of claim 2, wherein said first or second colored material (101, 102) is an ink.

4. The method of claim 3, wherein said ink is deposited by screen printing transfer.

5. The method of claim 2, wherein at least one of said first and second colored material is fluorescent, phosphorescent or radio-opaque.

6. The method of claim 2, wherein said first substrate layer (100) or said second substrate layer (200) or any of said first and second colored materials (101, 102) is composed of a soft material.

7. The method of claim 6, wherein said soft material is an intrinsically elastic material.

8. The method of claim 2, wherein said first colored material (101) and said at least second colored material (102) have different colors.

9. The method of claim 1, wherein said first colored material (101) is deposited onto said first substrate layer (100) to provide a shape label, a number label, a letter label, a barcode label, a QR-code label, an alignment or tracking mark, a background serving as a projection screen or a color label.

10. The method of claim 1, wherein said labelling portion is located in correspondence of a functional element of the device (300).

11. The method of claim 10, wherein said functional element is selected from a list comprising an electrode, an electrode array, a conductive track, a pad, a thru via, a microchip, a reservoir, a connector, a light emitting device, a microfluidic channel, a microfluidic outlet, an array of microfluidic outlets, a mechanical transducer, a chemical sensor and an optical device.

12. A method for labelling a portion of a device (300), said method comprising the steps of:
- Providing a first substrate layer (100) of a transparent or translucent material;
- Depositing a first colored material (101) onto said first substrate layer (100) in a labelling portion of said first substrate layer, thereby obtaining a labelling item (1000);
- Applying a second substrate layer (200) onto said first colored material (101) and said first substrate layer (100); and
- Coupling said labelling item (1000) to the device (300), wherein said device (300) is manufactured onto said second substrate layer (200).

13. The method of claim 12, wherein the second substrate layer (200) is made of a transparent or translucent material.

* * * * *